United States Patent [19]

Feitler et al.

[11] Patent Number: 4,675,410

[45] Date of Patent: Jun. 23, 1987

[54] PROCESS FOR THE PRODUCTION OF PYRIDINE OR ALKYL SUBSTITUTED PYRIDINES

[75] Inventors: David Feitler, New Windsor; Wolfgang Schimming; Henry Wetstein, both of Monroe, all of N.Y.

[73] Assignee: Nepera Inc., Harriman, N.Y.

[21] Appl. No.: 848,891

[22] Filed: Mar. 21, 1986

Related U.S. Application Data

[63] Continuation of Ser. No. 512,834, Jul. 11, 1983, abandoned.

[51] Int. Cl.$^4$ .................... C07D 213/8; C07D 213/9; C07D 213/10
[52] U.S. Cl. ................................. 546/251; 546/250
[58] Field of Search ............................. 546/250, 251

[56] References Cited

U.S. PATENT DOCUMENTS

| | | | |
|---|---|---|---|
| 2,807,618 | 9/1957 | Cislak et al. | 546/253 |
| 3,728,408 | 4/1973 | Tobias | 568/822 |
| 3,894,106 | 7/1975 | Chang et al. | 585/408 |
| 3,894,107 | 7/1975 | Butter et al. | 585/408 |
| 3,946,020 | 3/1976 | Minato et al. | 502/263 |
| 4,071,573 | 1/1978 | Owen et al. | 423/585 |
| 4,147,874 | 4/1979 | Beschke et al. | 546/251 |
| 4,149,002 | 4/1979 | Beschke et al. | 546/251 |
| 4,220,783 | 9/1980 | Chang et al. | 546/251 |
| 4,268,420 | 5/1981 | Klotz | 252/232 |
| 4,269,813 | 5/1981 | Klotz et al. | 423/277 |
| 4,285,919 | 8/1981 | Klotz et al. | 423/277 |
| 4,292,457 | 9/1981 | Klotz | 585/447 |
| 4,292,458 | 9/1981 | Klotz | 585/469 |

FOREIGN PATENT DOCUMENTS

| | | | |
|---|---|---|---|
| 1931945 | 1/1971 | Fed. Rep. of Germany | 546/251 |
| 1670514 | 3/1972 | Fed. Rep. of Germany | 546/251 |
| 2051316 | 4/1972 | Fed. Rep. of Germany | 546/251 |
| 2203384 | 8/1973 | Fed. Rep. of Germany | 546/251 |
| 1182705 | 3/1970 | United Kingdom | 546/251 |

OTHER PUBLICATIONS

"Heterogeneous Conversion of Acrylic Compounds to Pyridine Bases—A Review", *Applied Catalysis*, 23, (1986), 1–14.

*Primary Examiner*—Alan L. Rotman
*Attorney, Agent, or Firm*—Millen & White

[57] ABSTRACT

A process for preparing pyridine or alkyl substituted pyridines in high yield, comprises reacting a $C_{2-5}$-aldehyde, a $C_{3-5}$-ketone or a mixture thereof, ammonia and, optionally, formaldehyde, in the gas phase in contact with a fluidized or otherwise movable bed of a catalytically effective amount of a crystalline aluminosilicate zeolite catalyst in the acidic form and having a constraint index of about 1 to about 12, with an actual contact time of the reactants with the catalyst which is at least as great as said actual contact time when the reaction is conducted in a 1 inch diameter fluid bed reactor with a pseudo contact time of at least about 2.5 seconds.

21 Claims, No Drawings

PROCESS FOR THE PRODUCTION OF PYRIDINE OR ALKYL SUBSTITUTED PYRIDINES

This application is a continuation of application Ser. No. 512,834 filed July 11, 1983, now abandoned.

BACKGROUND OF THE INVENTION

This invention relates to an improved gas phase process for preparing pyridine and/or alkyl-substituted pyridines in high yields of main product, e.g., pyridine, and, preferably, with low or desirably regulated amounts of side products, e.g., often the picolines, by reacting at least one carbonyl compound and ammonia in the presence of a silica/alumina catalyst. One particularly preferred process is the preparation of pyridine by the gas phase catalytic condensation of acetaldehyde, formaldehyde and ammonia.

Such reactions have hitherto been carried out over a variety of catalysts containing silica and alumina, both crystalline and amorphous, and using a variety of reactant combinations, e.g., in addition to aldehydes, ketones and ammonia, also alcohols, water, etc.

Predominantly, the prior art catalysts have been amorphous in structure. See, e.g., U.S. Pat. Nos. 3,272,825; 3,946,020; 2,807,618; and 4,089,863; Japanese Patents Nos. 76-63,176; 71-41,546; 69-32,790; 80-151,558; and 80-151,559; Great Britain Patent No. 1,141,526; German Patent No. 2,203,384; and East German Patent No. 130,784, among many others. Such amorphous catalysts have been employed in both fixed and fluidized bed reactors without any significant differences in product yields and/or ratios of main products to side products. The yields of desired products have heretofore been unsatisfactory.

On the other hand, crystalline aluminosilicate catalysts, including those having a constraint index of about 1 to about 12 and a silica to alumina ratio of greater than about 10-12, have also been utilized in such reactions. See, e.g., U.S. Pat. No. 4,220,783 and U.S. Pat. No. 3,728,408 (e.g., column 25, line 23). However, these reactions have been carried out only in fixed catalyst beds. Once again, the resultant yields of desired products have been unsatisfactory. Moreover, in order to optimize the ratio of desired product to undesired side products, there is invariably a concomitant decrease in overall product yield; conversely, if the overall product yield is increased, there is a concomitant decrease in ratio of desired product to undesired product. For example, for the prior art reactions of acetaldehyde, formaldehyde and ammonia, the total molar yield of pyridine and $\alpha$- and $\beta$-picolines, based on 2 moles of acetaldehyde reactant, varies within the range of 35-72 molar percent while the weight ratio of desired pyridine to undesired picoline side products, expressed as the weight ratio of pyridine to $\beta$-picoline, varies inversely, in the range of 1.2-3. Yields have been somewhat higher in the crotonaldehyde/formaldehyde/ammonia system but unsatisfactory ratios of desired to undesired products and unsatisfactory overall results are still obtained. See, e.g., German patents Nos. 1,931,945 and 2,051,316. There remains a need to improve these results in favor of the desired product which is pyridine.

Heretofore, the nature of the catalyst bed (fixed or fluidized or otherwise movable), has not been a factor in increasing yield of desired product. In general, fixed beds are employed in these catalytic reactions unless the additional expenditures associated with a fluidized bed are warranted by system-specific considerations. As is well known, (See, e.g., "Fluidized Bed Technology" by Zenz, in Kirk-Othmar, Encyclopedia of Chemical Technology, 2nd Edition, Volume 9, page 398 ff.), fluidized beds are of advantage when temperature control is a particular problem in the reaction or where catalyst coking is a particular problem, i.e., where catalyst regeneration must be facilitated.

In the past, fluidized or otherwise movable beds have been used in conjunction with the underlying reactions involved in this invention only when amorphous aluminosilicate catalysts are employed since these have coking problems attendant to their use. See, e.g., U.S. Pat. Nos. 2,807,618 (column 1); 3,946,020 (column 2); 4,147,874 (column 2); 4,149,002 (column 2); DT No. 2,203,384; and DS No. 1,670,514, among many others. Fluidized bed reactors have not been employed in the reactions involved herein using the required crystalline catalysts since the latter are known to be associated with exceptionally low coke deposits. (See, e.g., Dejaifve et al, Journal of Catalysis 70, 123-136 (1981); Walsh et al, Journal of Catalysis 56, 195-197 (1979); Cormerais et al, Zeolites, 1981, Vol. 1, October, 141-144; Derouane et al, Applied Catalysis, 1 (1981) 201-224; E. G. Derouane, Catalysis by Zeolites, B. Imelik et al. (Editors), 1980, Elsevier Scientific Publishing Company, Amsterdam, 5-46; all of whose disclosures are entirely incorporated by reference herein as they relate to the catalysts employed in this invention.)

Another factor in the prior art use of fixed beds is that only the reactions of this invention are known to be relatively temperature insensitive. See, e.g., examples 6 and 10 below. In this regard, see also U.S. Pat. No. 4,071,573 which employs the same crystalline aluminosilicate catalysts mentioned above in a different reaction but in a unique fluidized bed design since the reactions involved have associated therewith a need for disposal of the exothermic heat of reaction which otherwise is detrimental, especially to the catalyst lifetime. See also U.S. Pat. Nos. 3,894,106 and 3,894,107 each of which discloses the equivalent use of such crystalline catalysts in fixed or fluidized beds in conjunction with different reactions. Note, in particular, column 7, lines 23-32 and column 9, lines 50-64 respectively.

As can be seen, as is generally the case, except for specific system considerations which might dictate a preference for fixed versus fluidized or otherwise movable beds in a given reaction, in general, the two are expected to produce equivalent results. Particularly with reference to the class of reactions to which this invention relates, the two types of beds have been shown to produce essentially equivalent results in the past. This is not unusual. Similar equivalencies have been observed in other systems. For example, in the ammoxidation of propene to acrylonitrile, Barbouteau et al (Chem. Eng. J. (Lausaune), 20, 43 1980); CA: 943737x), found that a fluid bed having a tube of a diameter twice that of a fixed bed reactor produced comparable results. The same research group investigated the oxidation of butane to maleic anhydride and found that under a narrow range of conditions, the fluid bed gave better selectivities than a fixed bed; however, under the broader range of conditions, the results were comparable. (Laguerie et al, Chem. Eng. J. (Lausaune) 5, 33 (1973); CA: 79:20928t.) As another example, the catalytic cracking of gas-oil was examined in the past, and catalyst life and selectivity were shown to be equivalent while conversion was always higher in the fixed bed.

Gross et al in Ind.Eng.Chem. Process R.Dev., 13, 199 (1974); CA 82:100966.

Thus, for the reaction to which this invention relates, there is a prior art expectancy that fixed and fluidized or otherwise movable beds will give essentially equivalent results when a crystalline aluminosilicate zeolite catalyst is employed, i.e., that the desired yields cannot be improved by carrying out the prior art fixed bed reaction in a fluidized or otherwise movable bed.

SUMMARY OF THE INVENTION

Accordingly, it is an object of this invention to provide an improved process for reacting a carbonyl compound with ammonia, in the gas phase, to produce pyridine-type bases having desirable increased yields and desirable ratios of desired products to undesired products.

It is another object of this invention to provide such a process which uses advantageous reactants, catalysts and reaction conditions.

It is yet another object of this invention to provide such a process which gives a latitude in selecting the ratio of individual products, preferably by selection of an easily varied reaction parameter.

Upon further study of the specification and appended claims, further objects and advantages of this invention will become apparent to those skilled in the art.

These objects have been achieved by providing a process for preparing pyridine and alkyl substituted pyridines in high yield, comprising reacting a $C_{2-5}$-aldehyde, a $C_{3-5}$-ketone or a mixture thereof, ammonia and, optionally, formaldehyde, in the gas phase in contact with a fluidized or otherwise movable bed of a catalytically effective amount of a crystalline almunosilicate zeolite catalyst in the acidic form and having a constraint index of about 1 to about 12, with an actual contact time of the reactants with the catalyst which is at least as great as the actual contact time of the reactants with the catalyst when the reaction is conducted in a 1 inch diameter fluid bed reactor with a pseudo contact time of at least about 2.5 seconds.

These objects have also been achieved based on the discovery of this invention that, using the process described above, the reaction can be carried out in a routinely determinable temperature range at which desired yield values and desired values of the ratio of main product to side product are essentially constant. Furthermore, it has been discovered that, typically, the reaction can be conducted at a temperature higher than this range at which lower total product yields will be achieved but with significantly higher ratios of main product to side product. Thereby, the overall yield of main product remains at essentially the same unexpectedly high level.

DETAILED DISCUSSION

The reactants employable in the condensation reaction of this invention include $C_{2-5}$-aliphatic aldehydes which can be saturated or unsaturated and/or $C_{3-5}$-aliphatic ketones which can also be saturated or unsaturated in admixture with ammonia. Formaldehyde is an often preferred coreactant. A single aldehyde, a single ketone, mixtures of aldehydes, mixtures of ketones and mixtures of aldehydes and ketones may be employed. Depending upon the precise combination of reactants employed and the stoichiometry, various main product pyridine-type bases and combinations of such main products with side products can be achieved, as is well known. For example, the following table lists some of the many possibilities.

A particularly preferred feed is the combination of acetaldehyde, formaldehyde and ammonia. Another preferred feed is the combination of crotonaldehyde, formaldehyde and ammonia.

The carbonyl compounds may be used as monomers, dimers, trimers, other oligomers or polymers, e.g., solid polymers, etc. Water can also be included in the reactant stream. For example, formaldehyde can be added to the reaction medium in the form of formalin, the water content of which is non-critical. Any conveniently available formalin, e.g., 10% formaldehyde, 50% formaldehyde, 90% formaldehyde, etc., can be employed. Also usable are the paraformaldehydes, s-trioxane, paracetaldehyde etc. Reactants are of ordinary commercial purity.

| Feed + NH$_3$ | Principal Product |
| --- | --- |
| 2 acetaldehyde + 1 formaldehyde | pyridine + $\beta$-picoline |
| 1 crotonaldehyde + 1 formaldehyde | pyridine + $\beta$-picoline |
| 2 acrolein | $\beta$-picoline + 3,5-lutidine |
| 1 acrolein + 1 acetaldehyde | pyridine + $\beta$-picoline |
| 1 acrolein + 1 acetone | pyridine + $\alpha$-picoline + $\beta$-picoline |
| 1 acrolein + 1 propionaldehyde | $\beta$-picoline + 3,5-lutidine |
| 2 propionaldehyde + 1 formaldehyde | 3,5-lutidine |
| 1 butyraldehyde + 1 acetaldehyde + 1 formaldehyde | 3-ethyl pyridine |
| 2 butyraldehyde + 1 formaldehyde | 3,5-diethyl pyridine |
| 3 acetaldehyde | $\alpha$- + $\beta$- + $\gamma$-picoline |

Molar ratios of the reactants for any given combination are routinely determinable in accordance with the underlying stoichiometry of the reaction. For example, the molar ratio of acetaldehyde: formaldehyde: ammonia is usually within the following approximate limits, based upon the monomeric aldehydes per se—1:0.6–3:0–.5–5; preferably 1:0.75–1.25:1–3. Typically, these molar ratios are 1:0.75–1:1–1.56. When water is included, generally, the molar ratio of water to acetaldehyde is up to 10, i.e., generally 0–10, usually 0–3. The amount thereof is essentially non-critical unless unreasonable dilutions are involved. For other feed combinations, analogous preferred molar ratios will be employed taking into account the ordinary conventional considerations.

The manner of mixing the gaseous reactants is also non-critical. Typically, for the preferred feed, the acetaldehyde and formaldehyde are added as a preformed mixture to the reactor. The ammonia is usually separately added. The manner of all additions is fully conventional.

Normally, it is preferred to carry out the reaction in the absence of O$_2$, e.g., air. Otherwise, difficult controls may be necessary to avoid explosive mixtures. Of course, if necessary or desirable, the reaction can be conducted in the presence of a small amount of air. Similarly, it is preferred that the reaction be conducted in the presence of only the mentioned reactants. Of course, other inert, system compatible materials may also be present. One such compound, often used in the past is methanol. In many prior art cases, the alkanol has been used as a reactant, e.g., as a substitute for formaldehyde. However, in the reaction of this invention and also in some of the prior art reactions in which it was thought to be an active participant, methanol (and other alkanols for that matter) is inert with respect to pyridine and picoline products.

A critical feature of this invention is the performance of the process in a fluidized or otherwise mobilized bed of the catalyst. See, e.g., "Fluidized Bed technology" by Zenz, in Kirk-Othmar, Encyclopedia of Chemical Technology, 2nd Edition, Volume 9, page 398 ff., whose disclosure is incorporated by reference herein. Such a bed very surprisingly enables achievement of the heretofore unachievable high product yields, and, where appropriate, high ratios of desired main product to undesired side products which characterize this invention.

In other words, it has been found that the reaction of carbonyl compounds and ammonia over a crystalline aluminosilicate zeolite catalyst in the acidic form and having a constraint index of about 1 to about 12, will, completely unexpectedly, produce superior results—most notably, superior yields of desired product in comparison with the yields obtainable when the same reaction is conducted in a fixed bed, for example, as conducted in U.S. Pat. No. 4,220,783. In other words, the fluidized or otherwise mobilized bed reaction of this invention will always produce unexpectedly superior results vis a vis the same reaction carried out in a fixed bed under corresponding conditions. It has furthermore been discovered that these unexpectedly superior product characteristics can be achieved as long as a sufficient contact time between reactant and catalyst bed is maintained in the fluid bed reactor. Precise minimum contact times for a given system, including a particular reactant combination, particular bed diameter, particular flow rates, particular catalyst charges, etc. will be determined for each system by skilled workers using fully conventional considerations in combination with this disclosure, perhaps with a few routine preliminary experiments. The selection of a satisfactory minimum contact time will be facilitated by the following guidelines discussed in terms of "pseudo contact time ($CT_{ps}$)" in a fluidized bed system.

It is not possible to accurately calculate the real contact time involved in a given fluid bed system because of the deviations from ideal plug flow which occur in fluid beds, e.g., due to backmixing effects and other deviations from ideality; which cause the actual contact time generally to be longer. However, for purposes of definition and comparison, using a plug flow assumption, a pseudo contact time may be used to describe the lower limit on the actual contact time achieved in operation. The "pseudo contact time" may be defined as follows:

$$CT_{ps} = \frac{\text{working void volume}}{\text{total feed volume/sec}}$$

The working void volume may be calculated by adding the void volume of the unexpanded bed (typically 10–30 vol %) and the difference in volume between the expanded bed and the unexpanded bed. Alternatively, the working void volume may be calculated as the product of the unit void volume and the weight of the catalyst. The unit void volume is readily calculable by subtracting the reciprocal of the piece density of the catalyst from the reciprocal of the expanded bed density. Typically, unit void volumes are in the range of 0.5 to 3.0. For example, spray dried pentasil zeolites in a kaolin binder have a unit void volume of 1.21 cc/g. The denominator of the quotient defining $CT_{ps}$ is the total volume flow of the entire feed including ammonia and other optional ingredients such as water per second.

In a 1 inch diameter fluid bed reactor, such as that described below, it has been found that a pseudo contact time greater than approximately 2.5 seconds will ensure achievement of the superior results of the process of this invention as described above. Of course, in real time operation, the actual contact time of the reactants with the catalyst bed will be longer. By designing any fluid bed system to have an actual contact time equivalent to that provided by a pseudo contact time of about 2.5 seconds in a 1 inch diameter fluid bed reactor, an actual contact time corresponding to that necessary to achieve the superior results of this invention will, in fact, be obtained.

The minimum value of 2.5 seconds will vary somewhat from system to system in dependence upon the usual factors such as the amount of catalyst, the bed type, size and volume, the catalyst particle size, flow rates, packing density, bed characteristics such as grid sizes, numbers and sizes of zones and baffles, etc. When all of these routine design parameters are taken into account and the resultant pseudo contact time calculated in conjunction with routine preliminary experiments, a value of approximately 2.5 seconds in a 1 inch diameter reactor will ensure the superior results of this invention described above. Generally, in larger reactors lower pseudo contact times will suffice due predominantly to the relatively larger degree of backmixing which is encountered.

The precise value of minimum contact time will also vary to a minor extent in dependence upon the details of the reactants used in the feed. Again, a satisfactory minimum value for a given overall system, in the range of approximately 2.5 seconds for a 1 inch reactor, will be routinely determinable by those skilled in the art.

In general, the contact times actually employed in a preferred operation will be greater than the minimum contact time corresponding to the minimum pseudo contact time of 2.5 seconds as defined above. Typically, preferred pseudo contact times in a 1 inch reactor used will be about 3.5 seconds or even higher.

The throughput for the process of this invention generally will correspond to a weight hourly space velocity in the range of 0.1–10 the optimum values being routinely determinable conventionally and chosen to ensure the desired pseudo contact time in accordance with the foregoing. Typically, the reaction is conducted at pressures of 0.1–100 atm, generally 1–10 atm, preferably at 1 atmosphere.

In general, the process of this invention will provide a total product yield significantly higher than that achievable when running the same reaction in a fixed bed. For example, using a feed of acetaldehyde, formaldehyde and ammonia, total product yields of more than 75 molar percent, based on the number of moles of starting material acetaldehyde, will be attained, typically 75–90, and often 85–90 molar percent or higher. The total molar yields used throughout this application include the principal products, e.g., for the acetaldehyde/formaldehyde or crotonaldehyde/formaldehyde feeds, pyridine and α- and β-picoline are included. Analogously high total product yields will be attained for other feed combinations. For the latter, the products will often include other related alkyl pyridines such as any of the picolines, collidines, ethylpyridine, lutidines, etc.

The process of this invention also produces unexpectedly favorable ratios of desired main products to undesired side products. For example, in the acetaldehyde/- formaldehyde or crotonaldehyde/formaldehyde cases, the primary product is pyridine and the primary side product is usually $\beta$-picoline. Consequently, herein, the "ratios" refer to this most relevant ratio, i.e., the weight ratio of pyridine to $\beta$-picoline. This invention provides ratio values in the range of about 1.8–2.5, e.g., 2.0–2.3, etc. for the acetaldehyde/formaldehyde feed. Analogously high ratios will be attained for other feed combinations where applicable. These heretofore unachievable combinations of high total product yields and high ratios of desired main products to undesired side products represent a significant improvement over the best available state of the art results.

In another unique aspect of this invention, it has been found that the reactions can be conducted in a certain temperature range over which the total product yields and the ratios will be essentially constant, e.g., will differ by about ±5% or so. This region of relative temperature insensitivity provides a significant advantage for the process of this invention since precise temperature control will not be necessary as long as the reaction temperature stays within the relatively broad range within which essentially constant yields and ratios are achieved. For example, for the acetaldehyde/formaldehyde feed, the range will normally span about 50° C. within the range of 425°–500° C. in dependence upon the precise process conditions used. For the crotonaldehyde/formaldehyde feed, the temperature insensitivity range is even broader, spanning at least about 390°–450° C. Precise limits of this temperature insensitivity range will be routinely determinable for any given system within the scope of this invention by a few routine preliminary experiments. The primary determinant in this regard will usually be catalyst properties such as $SiO_2/Al_2O_3$ ratio; acidity; etc.

It has furthermore been found that the process of this invention will permit desirable adjustments in the ratio of products which are obtained. For example, normally, it will be desired to operate within the temperature insensitivity range. However, under certain circumstances, e.g., for economic considerations related to the relative costs of starting materials, product pyridine and product alkylpyridines, etc. it may be desired to operate at somewhat lower total product yields but at higher weight ratios of main product to undesired side products, e.g., as typified by the pyridine/$\beta$-picoline weight ratio defined above. Surprisingly, and advantageously, this invention provides a relatively simple means for achieving this end, viz., by simply operating at a temperature higher than the range defined above within which essentially constant yields and ratios are achieved. At these higher temperatures lower values of total product yields but higher ratios of desired main product to undesired side products will typically be attained. Thus, in the acetaldehyde/formaldehyde case, the yields achieved are somewhat less than about 75 wt %, e.g., about 70 to 75 wt %, but the ratios are greater than about 2.3–2.5, typically 2.6–5 or more. These unique combinations of yields and ratios are achieved for this particular feed system in the range of about 475°–650° C. Again, the precise high temperature used in this mode of the invention will be routinely selected by skilled workers using a few preliminary experiments in conjunction with conventional considerations regarding the desired combination of yield and ratio for a given reactant feed combination, the catalyst details, etc.

As can be seen, temperature is a convenient variable by which the process of this invention can be advantageously modified to provide a wide range of total product yield and ratio combinations. Where lower temperatures are preferred, e.g., for reasons of economy, the process is especially advantageous since results which are better than those achievable by the state of the art can be attained using temperatures lower than those required in the state of the art processes. At the same time, even under these advantageous conditions, there is the further advantage that fewer byproducts are produced, thereby considerably decreasing the necessary expenditures in time and effort for disposal thereof.

The mentioned temperature ranges, yield and ratio ranges, and pseudo contact times, are not meant to define strict end points for delineating the operating regions of this invention. Rather, they are provided as valuable guidelines for skilled workers—precise values for a given system being routinely determinable as discussed herein. For example, temperatures, yields and ratios for the various regimes may overlap from system to system within the scope of this invention.

As is usual for reactions of this type, conversions, e.g., based upon the amount of acetaldehyde used in the acetaldehyde/formaldehyde feed, are essentially 100%. Such optimized conversions can readily be attained by variation of the usual important parameters, most notably by ensuring that a sufficient amount of catalyst and a sufficient contact time are provided.

As mentioned above, the catalyst required by the process of this invention must have a constraint index of about 1 to about 12 and must be in the acidic form. Generally, the pore size will be greater than 5.5 Å.

"Constraint index" is a conventional term of art which is defined, e.g., in Frillette et al, Journal of Catalysis, 67, 218–222 (1981), whose disclosure is entirely incorporated by reference herein. This parameter is fully sufficient to define those catalysts which will have a microstructure suitable for use in the process of this invention, i.e., it defines those catalysts having pore characteristics such that the necessary constrained access to the interior of the catalyst is provided.

Constraint index (C.I.) values for some typical zeolites are given in the table below.

| Aluminosilicate | Constraint Index |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Clinoptilolite | 3.4 |
| S-115 | ~1 |
| Beta | 0.6 |
| Zeolite Omega | 0.5 |
| H-Zeolon (mordenite) | 0.4 |
| REY | 0.4 |
| Amorphous Silica-Alumina | 0.6 |
| Erionite | 38. |

Catalysts having such constraint indices are readily commercially available. For example, the ZSM catalysts are available for rent from Mobil Oil Corporation, New York, N.Y., and are discussed in detail in U.S. Pat. Nos. 3,702,886 (ZSM-5); 3,709,979 (ZSM-11); 3,832,449 (ZSM-12); 4,016,245 (ZSM-35); and 4,046,859 (ZSM-38), as well as U.S. Pat. Nos. 3,894,106 and 3,894,107. Also satisfactory will be those ZSM catalysts discussed in U.S. Pat. Nos. 4,209,499 (ZSM-43); European Patent Application Publication No. 0023089A1 (ZSM-48); and U.S. Pat. No. 4,229,424 (catalyst having a structure intermediate between that of ZSM-5 and ZSM-11). Also suitable for use in the process of this invention will be the silica polymorph "silicalite" class of catalysts of Union Carbide Corporation, New York, N.Y., which have the properties required by this invention, e.g., as disclosed in U.S. Pat. No. 4,061,724, e.g., S-115. All of the disclosures of the above-mentioned references are incorporated by reference herein.

In addition to the constraint index requirement, it is also necessary that the crystalline aluminosilicate zeolite catalyst of this invention be in the acidic form. Herein, "acidic" is taken to mean that at least 10% of the catalytic sites which are available to hydrogen ions are in fact occupied by hydrogen ions, hydronium ions, or some other form of acidic species having Bronsted acidity. Preferably, 10-100% of such sites are occupied by hydrogen ions or other species, most preferably 80-100% since, generally, the higher the acidity, the higher will be the ratio of pyridine to $\beta$-picoline at low temperatures. Catalysts having such acidities are readily commercially available, e.g., from the above-mentioned commercial sources. In any event, any zeolite otherwise meeting the requirements of this invention can be treated to achieve the necessary acidity by fully conventionally exchanging it, e.g., in the presence of an acid such as aqueous hydrogen chloride or $NH_4Cl$ etc. followed by conventional calcination in air at about 600°-800° C. for about 8 hours. See, e.g., Rajadhyaksha et al, J.Cat. 63, 510 (1980), and references cited therein, whose disclosures are entirely incorporated by reference herein.

Acidities as defined above can be fully conventionally determined, e.g., using the method described in Auroux et al, J.C.S.Faraday Trans. 1, vol II part II, 2544 (1979) and Vedrine et al, J.Cat. 59, 248 (1975) whose disclosures are entirely incorporated by reference herein.

Often, the various zeolites mentioned above or others, will be prepared in the presence of organic cations and hence, will be inappropriate for use in this invention, e.g., because they are catalytically inactive due to the presence of the organic cations. Presumably, this is caused by the occupation of the intracrystalline free space by such cations. These catalysts can be activated by conventional heating to higher temperatures in an inert atmosphere or vacuum, which is well known to result in the thermal destruction or removal of such organic cations. Moreover, it is often possible to convert natural zeolites to zeolitic catalysts which are suitable for use in this invention. This can be accomplished by various conventional activation procedures or other equivalent treatments, including base exchange, steaming, alumina extraction, calcination, combinations of the foregoing, etc. Natural minerals susceptible to such treatments include ferrierite, brewsterite, stilbit, dachiardite, epistilbite, heulandite, and clinoptilolite.

All of the crystalline catalysts mentioned above will thus be useful for the process of this invention as long as they have a constraint index within the mentioned range and an acidity within the mentioned range. These properties will be sufficient to guarantee the successful performance of the reaction of this invention. In part these characteristics are those necessary for a catalyst which is capable of sustaining the conversion of a hydrocarbon such as methanol to gasoline.

The catalysts suitable for use in this invention are also understood to include not only crystalline aluminosilicate zeolite catalysts possessing x-ray crystallinity but also those possessing x-ray amorphism but possessing infrared crystallinity as defined and disclosed in Jacobs et al, J.C.S.Chem Comm , 1981, 591–593, whose disclosure is entirely incorporated by reference herein. Similarly, the suitable catalysts are understood to include those in which various, usually trivalent, metals, e.g., boron, are apparently substituted for at least a portion of the aluminum in the crystal structure e.g. boron, arsenic, antimony, vanadium, iron or chromium. Such catalysts include those disclosed in DOS Nos. 28 30 787, 28 30 830, 28 31 611, 28 31 630, 28 31 631, and 29 09 929. Such catalysts can even no longer contain aluminum. (DOS No. 2830787—examples 1-6, 12 and 13: 100 mole % Al, examples 7-8: 100 mol % B, example 9: 100 mol % As, example 10, 100 mol % Sb; DOS No. 2831611—example 1: 75 mol % Fe, example 2: 85 mol % Fe, example 3: 90 mol % Fe; DOS No. 2831630—example 1: 58 mol % Cr, Example 2: 72 mol % Cr, Example 3: 83 mol % Cr; DOS No. 2831631—Example 1: 65 mol % V; DOS No. 2830830—38 mol % As; DOS No. 2909929—75 mol % B).

The catalysts suitable for use in the process of this invention will generally have $SiO_2Al_2O_3$ ratios in the range of 12–1000, e.g., 12–700, more preferably 18–400, and most preferably 200–400, often about 350. Catalysts having such low amounts of aluminum are active for the process of this invention as long as the foregoing characteristics are met. The mentioned silica to alumina ratio can be fully conventionally determined using routine methods of analysis. See, e.g., Bibby et al, J. Catalysis, 72, 373–374 (1981), whose disclosure is entirely incorporated by reference herein. This ratio, as is fully conventional, refers, as closely as possible, to the ratio in the rigid crystalline framework of the zeolite crystal. The aluminum in the catalyst carrier or binder and in cationic or other form within the catalyst's channels, is excluded, as is well known.

The necessary and sufficient characteristics of the catalyst of this invention are those disclosed herein. Thus, any conventional interpretations of the term "zeolite" which might be inconsistent or more limiting than the definitions given herein are not relevant.

Other catalyst-related characteristics and parameters will be conventionally determined, e.g., in conjunction with the details of the fluidized or otherwise movable bed which is being used and the details of this application. Such characteristics include the volume of the catalyst bed, the relative amount of catalyst, the contact time, the particle size (which will usually be in the range of 20–120 m, preferably 45–100 m), the particle shape (which will not be critical to the yields and ratios described above and includes powders, granules, molded products such as extrudates, crushed particles, etc.), etc.

An example of the effect of one such variable, is presented below in example 8. As can be seen, by routine experimentation, the catalyst weight can be adjusted, and hence the effective contact time, to yield the superior yield/ratio values of this invention. The same is true for all other parameters.

Of course, since it is required that the process of this invention be carried out in a fluidized or otherwise movable bed, it is greatly preferred that the catalyst be used in the conventional form which is most suitable for such beds, e.g., in spray-dried form, having a preferred narrow particle size distribution of spherical particles;

in conjunction with a fluidized diluent (e.g., 0–50 weight percent) which will increase the bed volume and, hence, the contact time (See, e.g., Example 8, below.); having a density and sufficient physical strength to be retained in the customary arrangements of catalyst recovery devices (e.g., cyclones); and sufficiently resistant to abrasion, erosion and attrition to achieve a long retention life in the system. One preferred form of catalyst is a microsphere incorporating binder and catalyst. The microsphere may be solid, hollow or amphora like in structure. Technologies for preparation of such forms are conventional and are described, e.g., in A. G. Oblad, Oil & Gas Journal, 70 (13), 84 (1972), U.S. Pat. No. 3,450,680 and U.S. Pat. No. 3,140,249, whose disclosures are entirely incorporated by reference herein. The relative amounts of active catalyst and inert carrier or binder are not critical and can vary within a wide range, e.g. about 1–99% by weight of the carrier based upon the total weight of the combination. Usually, the amount of active catalyst is 5–80%, preferably 20–50% by weight of the composite.

Suitable such carrier or binder materials are fully conventional and include synthetic or naturally occurring substances as well as inorganic materials such as clay, silica and/or metal oxides. Suitable such substances are described, e.g., in U.S. Pat. No. 4,220,783, at column 6, lines 12–45, which disclosure is entirely incorporated by reference herein. Typically, the carrier will be a porous matrix, gel-like material such as alumina, silica-alumina, silica-magnesia, silica-zirconia, etc., as well as ternary such compositions including silica-alumina-thoria, silica-alumina-zirconia, silica-alumina-magnesia, silica-magnesia-zirconia, etc. The bound catalyst can also be extruded if desired. Binder and extrusion technology are fully conventional.

One of the surprising features of this invention is derived from the fact that the catalyst required involves very low coke formation in use. As discussed above, it is coke formation on various zeolytic catalysts which is usually a most important consideration dictating the use of a fluidized bed. Conventionally, it would be expected that a fluidized bed offers no distinct advantages over a fixed bed in a process such as that of this invention wherein the catalyst is known to be associated with only low coke deposits. In this regard, see the references mentioned in the foregoing Background section. Of course, when the minimal coking deposits do accumulate over time, the catalyst can be conveniently and routinely regenerated by conventional burning at conventionally high temperatures to restore catalytic activity.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, all temperatures are set forth uncorrected in degrees Celsius; unless otherwise indicated, all parts and percentages are by weight.

In the following, all of the yields and ratios are as defined above unless indicated otherwise. The catalysts utilized in the following examples have the properties shown in the table.

Each of the examples of this invention was conducted in a fluid bed reactor consisting of a stand pipe, a grid plate, and a one or two inch diameter vertical stainless steel tube 36 inches long. The catalyst disengagement section consisted of a vertical segment 18 inches long flared, over 4 vertical inches, to 4 to 6 inches in diameter. This eliminated the need for a cyclone. The grid plate consisted of 2 $\mu$m stainless steel mesh. Organic feeds were introduced through a port 4 inches above the grid plate while ammonia was introduced beneath it. All reactants were heated to a temperature between 200° and 400° C. before introduction into the reactor. In the 1 inch reactor, 270 g of catalyst was typically used. The bed volume for 270 g of pentasil catalyst in spray dried form was 473 cc, for example. In the two inch reactor, 1080 g of pentasil catalyst was typically used. The bed volume there was 1900 cc. Products were condensed using glass or metal water cooled condensers, at intervals of 30 or 60 minutes for periods of 3–6 hours. Liquid products were analyzed by gas chromatography using propanol, butanol or 2,6-lutidine as an internal standard. The gas chromatographic analysis used a 12 ft, ⅛ inch stainless steel column packed with 25% Triton X-305/2.5% NaOH or Chromosorb W 60/80 mesh.

All of the fixed bed experiments were conducted as described in Example 12.

EXAMPLE 1

1080 g of a spray dried catalyst formulation consisting of 40% catalyst VI and 60% kaolin/alumina was loaded into the 2 inch diameter fluid bed reactor. The catalyst was heated under a nitrogen flow of 60 liters per hour to a temperature of 450° C. A mixture of 1,054 g of acetaldehyde and 1,437 g of formalin (50% formaldehyde) was passed through a vaporizer (at a temperature of 120° C.) into the reactor at a flow rate of 430 cc/hr. The nitrogen flow into the reactor was replaced with an ammonia flow at a rate of 111 g/hr. These conditions provided a molar ratio of acetaldehyde:formaldehyde:ammonia:water of 1:1:1.5:1.66. The sample from the first 30 minutes of operation was discarded. Subsequent samples gave the results summarized below. The catalyst was regenerated by heating at 550° C. in an air flow of 60 l/hr. overnight.

| Time(minutes) | 30–60 | 60–120 | 120–180 | 180–240 |
|---|---|---|---|---|
| Yield | 82.8 | 89.8 | 87.0 | 83.6 |
| Pyridine/$\beta$-picoline | 2.13 | 2.07 | 2.18 | 2.19 |

In the following examples, the yields are the average molar yields based upon the values in the second and third columns above, i.e., they are the average yields calculated from the samples taken after 60–120 minute and 120–180 minutes of reaction. Here, the yield is 88.4.

The same reaction sequence was repeated several times using the same catalyst. After six such use/regeneration cycles, the results in the last cycle, using 932 g of catalyst were as follows:

| Time/minutes | 30–60 | 60–120 | 120–180 | 180–240 |
|---|---|---|---|---|
| Yield | 81.6 | 83.7 | 81.3 | 73.47 |
| Ratio | 2.19 | 2.29 | 2.41 | 2.45 |

All yields in this and other examples were determined conventionally using gas chromatographic analysis of the liquid products obtained in each sample as described above. The mentioned values were periodically confirmed by distillation.

In all of the following examples, the procedure employed was identical to that of this example unless noted otherwise.

| Catalyst # | C.I. | SiO$_2$/Al$_2$O$_3$ | Physical Form | Expanded Bed Density | Commercial Designation |
|---|---|---|---|---|---|
| I | ~1 | 350 | spray dried | 0.57 | S-115 |
| II | ~1 | 350 | spray dried | 0.47 | S-115 |
| III* | — | 10 | spray dried | 0.46 | Grace 135 |
| IV | 1-12 | 18 | extrudate-ground | — | ZSM 5 |
| V | 1-12 | 18 | extrudate-ground | — | ZSM 5 |
| VI | ~1 | 350 | spray dried | ~0.6 | S-115 |
| VII* | — | ~10 | spray dried | ~0.46 | Cat of 3946020 |
| VIII | 1-12 | ~300 | extrudate | — | S-115 |

*prior art

EXAMPLE 2

The procedure of example 1 was repeated except using the catalyst listed in the following table in the 1 inch reactor. As can be seen from these results, zeolites with constraint indices of 1-12 are superior to amorphous materials.

| | Catalyst | | | |
|---|---|---|---|---|
| | III* | I+ | I | VI |
| | Reaction Temperature | | | |
| PRODUCT | 500° | 500° | 450° | 450° |
| Pyridine | 100 | 100 | 100 | 100 |
| α-picoline | 2.6 | 1.7 | 0.9 | 1.1 |
| β + γ-picoline | 60.3 | 51.7 | 52.4 | 49.9 |
| Unknown | 0.97 | 0.4 | 0.11 | 0.35 |
| 2,3-lutidine | 1.9 | 2.7 | 1.8 | 1.99 |
| 3,4-ethylpyridine | 1.9 | 1.0 | 0.8 | 0.76 |
| 3,5-lutidine | 6.4 | 5.3 | 6.7 | 5.52 |
| collidines | 22.0 | 14.7 | 9.1 | 3.90 |
| Total non-Pyridine and non-picoline | 33.2 | 24.1 | 18.5 | 12.5 |
| Yield | 64.9 | 79.6 | 83.3 | 88.8 |
| pyridine/β-picoline | 1.70 | 2.0 | 1.98 | 1.96 |

*prior art + 40% catalyst I; 60% kaolin/alumina

EXAMPLE 3

The process of example 1 was repeated except using the catalyst and conditions summarized in the table below. Also summarized in the following table are the results obtained when precisely the same process under corresponding conditions was carried out in a fixed bed.

| Catalyst | T (C.°) | Yield | Ratio |
|---|---|---|---|
| FLUID BED | | | |
| A. 40% Catalyst I/ | 450 | 83.3 | 1.98 |
| 60% kaolin/alumina | 500 | 79.5 | 1.98 |
| B. 50% SiO$_2$/ | 450 | 87.4 | 2.0 |
| 50% of Catalyst II | | | |
| C. 40% Catalyst VI/ | 450 | 88.4 | 2.14 |
| 60% kaolin/alumina | | | |
| FIXED BED | | | |
| A. 40% Catalyst I/ | 500 | 63.4 | 1.76 |
| 60% kaolin/alumina | | | |
| B. 50% SiO$_2$/ | 436 | 71.4 | 1.93 |
| 50% of Catalyst II | | | |
| C. 40% Catalyst VI/ | 450 | 77.0 | 1.99 |
| 60% kaolin/alumina | | | |

As can be seen, the superiority of the reaction run in a fluidized bed to that run in a fixed bed is clear.

EXAMPLE 4

The conditions of example 1 were repeated except using the catalysts and formaldehyde/acetaldehyde feed ratios described in the following table.

| Catalyst | Formaldehyde/ acetaldehyde (molar) | T (°C.) | Yield | Ratio |
|---|---|---|---|---|
| FLUID BED | | | | |
| 40% Catalyst I/ | 1 | 500 | 79.5 | 1.91 |
| 60% kaolin/alumina | | 450 | 83.3 | 1.98 |
| | 0.75 | 500 | 67.9 | 2.55 |
| | | 450 | 73.3 | 2.34 |
| | 0.50 | 450 | 55.9 | 1.9 |
| FIXED BED | | | | |
| 30% Catalyst I/ | 1 | 500 | 64.4 | 1.89 |
| 70% kaolin/alumina | 0.75 | 498 | 64.8 | 2.31 |
| | | 454 | 64.7 | 2.21 |
| | 0.60 | 455 | 58.0 | 2.25 |

Again, the superiority of the reaction conducted in a fluidized bed is apparent even as a function of changes in relative feed composition.

EXAMPLE 5 (COMPARATIVE)

The procedures of example 1 were repeated except using the different catalysts and conditions indicated in the table below.

| Catalyst | T(°C.) | Yield | Ratio |
|---|---|---|---|
| FLUID BED | | | |
| Catalyst III | 450 | 56.3 | 1.51 |
| | 500 | 63.0 | 1.71 |
| FIXED BED | | | |
| Catalyst III | 450 | 60.8 | 1.49 |
| | 470 | 61.6 | 1.74 |

The results show that for a catalyst which is inappropriate for this invention, i.e., one lacking a constraint index of 1-12 and a Si/Al of 15-1000, the fixed bed results are better than or equal to the fluidized bed results, which is the normally expected result.

EXAMPLE 6

The procedures of example 1 were repeated except using the catalyst and conditions summarized in the table below.

| Catalyst | T (°C.) | Yield | Ratio |
|---|---|---|---|
| FLUID BED | | | |
| 220 g of a mixture of | 400 | 66.6 | 1.48 |
| 40% Catalyst I and | 450 | 83.3 | 1.98 |
| 60% kaolin/alumina | 500 | 79.5 | 1.98 |
| FIXED BED | | | |

-continued

| Catalyst | T (°C.) | Yield | Ratio |
|---|---|---|---|
| 30% Catalyst I and | 403 | 69.4 | 1.85 |
| 70% kaolin/alumina | 448 | 69.5 | 1.94 |
|  | 457 | 69.1 | 2.00 |
|  | 483 | 69.0 | 1.89 |
|  | 498 | 64.4 | 1.89 |
| 50% Catalyst VIII and | 392 | 67.2 | 1.85 |
| 50% SiO$_2$ | 420 | 69.4 | 1.87 |
|  | 440 | 65.6 | 1.91 |
|  | 462 | 67.2 | 1.85 |

As these data show, the reaction carried out in accordance with this invention has associated therewith a temperature range at which it is essentially as temperature insensitive as is the reaction when carried out in accordance with the prior art.

EXAMPLE 7 (COMPARATIVE)

Following the details of example 1 above, except where indicated otherwise herein, the amorphous silica/alumina catalyst of U.S. Pat. No. 3,946,020 (catalyst VII) having 87% silica and 13% alumina was employed. The catalyst was first treated for 1 hour at 100° C. using a 20% solution of ammonium chloride. The reaction was conducted at 500° C. The yield was 63.3% and the ratio of pyridine to $\beta$-picoline eas 1.66. The same reaction was repeated under identical conditions except using the mentioned silica/alumina catalyst without the heat treatment with ammonium chloride. The yield was 63.1% and the ratio was 1.53.

EXAMPLE 8

The procedures of example 1 again were utilized except using the catalyst and conditions summarized below. The 1 inch fluid bed reactor was used.

| Catalyst | wt. catalyst formulation (g) | wt. diluent (g)* | T (°C.) | Yield | Ratio |
|---|---|---|---|---|---|
| 1. Catalyst I 40% | 140 | 0 | 450 | 57.8 | 2.31 |
| Kaolin/alumina 60% | 180 | 0 | 450 | 68.8 | 2.13 |
|  | 220 | 0 | 450 | 75.6 | 2.02 |
|  | 270 | 0 | 450 | 81.3 | 1.93 |
|  | 288 | 0 | 450 | 84.5 | 1.89 |
| 2. Catalyst II 50% | 220 | 0 | 450 | 81.0 | 2.08 |
| Silica 50% | 260 | 0 | 450 | 87.4 | 2.00 |
| 3. Catalyst III** | 0 | 125 | 500 | 55.6 | 1.90 |
| (a control run) | 0 | 150 | 500 | 61.3 | 1.78 |
|  | 0 | 200 | 500 | 64.2 | 1.73 |
|  | 0 | 250 | 500 | 63.3 | 1.69 |
| 4. Catalyst I | 20 | 200 | 450 | 56.3 | 1.51 |
|  | 44 | 176 | 450 | 64.2 | 1.71 |
|  | 88 | 132 | 450 | 67.9 | 2.03 |
|  | 130 | 130 | 450 | 76.5 | 1.99 |
|  | 44 | 176 | 500 | 68.2 | 1.96 |
|  | 88 | 132 | 500 | 67.8 | 2.03 |
| 5. Catalyst II 50% | 52 | 208 | 450 | 69.7 | 1.71 |
| Silica 50% | 130 | 130 | 450 | 76.7 | 2.01 |

*Diluent was 85% silica/15% alumina (catalyst III of this table)
**Prior Art

As can be seen, inert or relatively inert fluidizable diluents can be used in the fluidized bed in accordance with this invention as long as appropriate conditions are observed. For example, in both cases, i.e., with and without a diluent, as is conventional in such reactions, there will be a certain relative weight of catalyst for which the reaction results will be optimized, including conversion, yield, ratio, etc. For a certain weight of catalyst, there will be associated a certain contact time in dependence upon the specific characteristics of the reactor. When an inert diluent is included, there will be no effect on the catalytic activity per se; however, as usual, since the bed volume thereby increases, the effective contact time (and pseudo contact time as defined above) will also increase. As a result of these longer contact times, for a given weight of catalyst, the reaction yield will be proportionately higher. This effect can be seen in the foregoing data, e.g., wherein 130 g of catalyst I bound to 40% kaolin and 20% alumina produces a yield of 76.5; whereas a similar yield is achieved using 220 g of the same catalyst without an inert diluent.

EXAMPLE 9

The details of example 1 were utilized except as indicated otherwise in the table below.

| Catalyst | T (°C.) | Yield | Ratio | |
|---|---|---|---|---|
| Catalyst I 40% | 425 | 85.0 | 2.30 | ⎫ |
| 60% kaolin/alumina | 450 | 85.0 | 2.24 | ⎬ Control Range |
|  | 475 | 84.4 | 2.29 | ⎭ |
|  | 500 | 78.1 | 2.66 | ⎫ |
|  | 525 | 72.3 | 2.85 | ⎬ Variable Range |
|  | 550 | 62.5 | 3.39 | ⎭ |

As can be seen, within a relatively broad temperature range, the yield and ratios remain essentially constant. As the temperature is raised outside of this range, the yield values decrease and ratio values increase. In the higher temperature regime, the amount of pyridine, however, which is a function of both the yield and the ratio, remains more or less constant at the higher temperatures. This provides a wide latitude in selecting process conditions to achieve high yields of pyridine. Accordingly, as market conditions vary, the process can be optimized from both operational and economic viewpoints.

EXAMPLE 10

The procedures of example 1 were repeated except for the changes shown in the table below.

| Catalyst | T(°C.) | Run # | wt. catalyst (g) | Yield | Ratio | % wt. loss* |
|---|---|---|---|---|---|---|
| | | | 1 inch reactor | | | |
| I | 450 | — | 260 | 84.7 | 2.05 | 3.4 |
| III** | 450 | — | 260 | 63.3 | 1.69 | 5.8 |

-continued

| Catalyst | T(°C.) | Run # | wt. catalyst (g) | Yield | Ratio | % wt. loss* |
|---|---|---|---|---|---|---|
| 2 inch reactor (run time: 4 hr.) | | | | | | |
| III** | 500 | 1 | 1080 | — | — | 7.2 |
| | 500 | 2 | 1080 | — | — | 7.7 |
| VI† | 450 | 3 | 1080 | — | — | 2.45 |
| | 450 | 4 | 1080 | — | — | 2.2 |

*on ignition of catalyst used
**prior art † 40% of catalyst; 60% kaolin/alumina

As can be seen, the catalysts employed in this invention coke to a significantly lesser degree than do prior art catalysts even when a fluidized bed is utilized. However, the improvement in coking upon changing from a fixed bed to a fluidized bed is much smaller for the catalysts used in this invention than for a prior art amorphous catalyst.

EXAMPLE 11

The procedures of example 1 were repeated except for the changes shown in the table below.

| Catalyst | T (°C.) | Yield | Ratio |
|---|---|---|---|
| FLUID BED | | | |
| 40% Catalyst I/ 60% kaolin/alumina | 450 | | 2.31 |
| Catalyst V* | 450 | 83.2 | 1.9 |
| | 500 | 76.4 | 2.8 |
| *1 inch reactor | | | |
| FIXED BED | | | |
| 40% Catalyst VI/ 60% kaolin/alumina | 470 | 77 ± 2.1 | 1.99 ± 0.07 |
| Catalyst VI without binder | 450 | 69.7 | 1.75 |
| Catalyst V without binder | 460 | 71.5 | 1.56 |

These data show the wide range of $SiO_2/Al_2O_3$ ratios over which the results of this invention are achieved.

EXAMPLE 12

Fixed Bed Operation

Catalyst VI (169 g) formulated at 30% with 70% kaolin/alumina, as a ⅛ inch extrudate was loaded into a tubular reactor having an inner diameter of 15.8 mm containing a thermowell of 6 mm OD and a free cross sectional area of 167 mm². The catalyst was purged under $N_2$ at 470° C. Nitrogen was replaced with ammonia at 14.33 g/hr. Acetaldehyde and formalin (45-55%) were fed at rates of 22 g and 31 g/hr., respectively. Under these conditions, 14 runs (3 hrs. each) were made, followed by regeneration in air at 550° C. overnight. The contact time for this series was 0.65 sec. No decline in catalytic activity was observed. The average yield was 77±2.1% and the average ratio was 1.99±0.07. These data are from the 60-120 minute interval as described in Example 1. Thus, they are higher than those which correspond to the average values used in the other examples, i.e., to the average of the 60-120 and 120-180 minute intervals.

EXAMPLE 13

Experiments were conducted as in Example 1 except that crotonaldehyde was used in place of acetaldehyde at a rate of 1 mole for every two of acetaldehyde. The following results show that the unexpected superiority of fluid bed results to fixed bed results extends to other carbonyl-containing feeds in general.

| | F/C Molar Ratio | Yield* | Ratio |
|---|---|---|---|
| FLUID BED 450° C. | | | |
| Catalyst VI | 2/1 | 75.0 | 5.6 |
| | 2.2/1 | 77.1 | 6.06 |
| | 2.4/1 | 80.5 | 6.0 |
| FIXED BED 400-500° C. | | | |
| 50% Catalyst (VIII) Extrudate | | — | |
| 50% $SiO_2$ Binder | | 38.9 | 2.34 |

*Average of 4 hrs. based on crotonaldehyde consumed.
F/C = formalaldehyde/crotonaldehyde

EXAMPLE 14

The process of this invention was conducted as in Example 1 except using one mole of crotonaldehyde for every two of acetaldehyde. The results show that like acetaldehyde, the crotonaldehyde reaction has a range of constant yield vs. temperature, and also is insensitive to formaldehyde content.

| Catalyst VI | | |
|---|---|---|
| | Yield | Ratio |
| F/C* = 2/1 | | |
| Temp. 420 | 78.5 | 4.3 |
| 450 | 77.3 | 5.6 |
| 500 | 56.4 | 6.8 |
| F/C = 2.2/1 | | |
| Temp. 420 | 79.4 | 5.0 |
| 450 | 80.5 | 6.0 |

Pseudo contact times were > ~3.5 sec.

| | Yield Profile (min) | | | | |
|---|---|---|---|---|---|
| F/C | 30-60 | 60-120 | 120-180 | 180-240 | % wt. loss** |
| | | | 450° C. | | |
| 2/1 | 79.2 | 79.4 | 78.9 | 72.9 | 3.5 |
| 2.2/1 | 83.8 | 80.2 | 76.2 | 71.3 | 4.0 |
| 2.4/1 | 87.0 | 83.9 | 79.7 | 74.6 | 3.6 |
| 2.6/1 | 85.3 | 84.8 | 78.5 | 73.0 | 3.81 |
| | | | 420° C. | | |
| 2/1 | 81.5 | 79.7 | 79.8 | 74.8 | |
| 2.4/1 | 84.8 | 83.6 | 79.4 | 73.2 | |
| | | | 390° C. | | |
| 2.4/1 | 85.5 | 85.1 | 78.6 | 69.6 | |

*F/C = formaldehyde/crotonaldehyde molar ratio
**on ignition of catalyst used

EXAMPLE 15

The process of Example was 1 repeated except as shown below. The results show the superior fluid bed yields of this invention are achieved regardless of catalyst form.

| | Yield | Ratio |
|---|---|---|
| Catalyst VI (Si/Al = 350) as Ground Extrudate | | |
| 30% Zeolite 70% Kaolin | 77.15 | 1.94 |
| 40% Zeolite 60% Kaolin | 80.26 | 2.08 |
| Catalyst VI (Si/Al = 350) as Spray-Dried | | |
| 40% Zeolite 40% Kaolin - 20% Alumina | 83.3 | 1.98 |

EXAMPLE 16

The process of Example 1 was repeated except as shown below. The results demonstrate the effect of contact time on the fluid bed results and show the type of routine preliminary experiments which can be used to determine when a satisfactory contact time is established.

| | Fluid Bed | | |
|---|---|---|---|
| Pseudo-Contact Time (sec) | Catalyst | Yield | Ratio |
| | 1 inch reactor* | | |
| 1.87 | I | 57.8 | 2.31 |
| 2.41 | I | 68.8 | 2.13 |
| 2.93 | I | 75.6 | 2.02 |
| 3.60 | I | 81.3 | 1.93 |
| 3.85 | I | 84.5 | 1.89 |
| | 2 inch reactor* | | |
| 3.85 | VI | 84.5 | 2.10 |
| 7.23 | VI | 84.5 | 2.44 |

*Contact time was varied by changing the amount of catalyst or the feed rate, respectively, in the 1 inch or the 2 inch reactor.

EXAMPLE 17

Using 240 g of a spray dried formulation (Catalyst VI 40%, kaolin/alumina 60%) in the one inch fluidized bed reator at 450°, mixtures of acrolein and acetone (2 moles total/hr) with one mole of ammonia per mole of organic reactant were fed to give the following usefule results:

| Mole Ratio | | | % Composition | | | |
|---|---|---|---|---|---|---|
| Acrolein | Acetone | % Yield* | Pyridine | Alpha | Beta | 2,6-Lu-tidine |
| 3 | 1 | 59.6 | 31.4 | 30.1 | 36.0 | 2.8 |
| 9 | 1 | 71.1 | 43.4 | 12.5 | 43.5 | 0.6 |
| 1 | 0 | 76.3 | 50.7 | 0.7 | 48.5 | — |

* $\frac{\text{Total moles of carbon in pyridine and Picolines}}{\text{Total moles of carbon feed}}$ While historical market conditions have encouraged the production of pyridine and $\beta$-picoline with high ratios of pyridine/$\beta$-picoline as the preferred mode of operation, changes in market conditions may dictate other preferred modes of operation. Thus, in the reaction of this example, presynthesis of acrolein from acetaldehyde and formaldehyde followed by reaction over a fluid catalyst bed can give superior yields with large amounts of $\beta$-picoline. Using mixtures of acetone and acrolein can lead to the inclusion of significant amounts of $\alpha$-picoline, with negligible amounts of $\gamma$-picoline, to contaminate $\alpha$-picoline.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing pyridine or alkyl substituted pyridines in high yield, comprising reacting a $C_{2-5}$-aldehyde, a $C_{3-5}$-ketone or a mixture thereof, ammonia and, optionally, formaldehyde, in the gas phase, the improvement comprising performing said reaction in contact with a fluidized or otherwise movable bed of a catalytically effective amount of a crystalline aluminosilicate zeolite catalyst in the acidic form and having a constraint index of about 1 to about 12 and a ratio of $SiO_2$ to $Al_2O_3$ of about 12–1000.

2. A process of claim 1 wherein the reactants are acetaldehyde, formaldehyde and ammonia and the main product is pyridine.

3. A process of claim 2 wherein the molar ratio of acetaldehyde:formaldehyde:ammonia is about 1:0.6–3:0.5–5.

4. A process of claim 2 wherein said ratio of reactants is about 1:0 75–1.25:1–3.

5. A process of claim 2 wherein water is also present in the reactant mixture up to an amount of 10 moles per mole of acetaldehyde.

6. A process of claim 1 or 2 wherein the ratio of $SiO_2$ to $Al_2O_3$ in the catalyst is about 18–400.

7. A process of claim 1 or 2 wherein the ratio of $SiO_2$ to $Al_2O_3$ in the catalyst is about 200–400.

8. A process of claim 1 or 2 wherein the ratio of $SiO_2$ to $Al_2O_3$ in the catalyst is about 350.

9. A process of claim 1 or 2 wherein the catalyst is in spray-dried form.

10. A process of claim 1 or 2 wherein said catalyst is mixed with a reaction compatible diluent.

11. A process of claim 1 wherein 80–100% of the catalyst sites available to hydrogen ions are occupied by hydrogen ions.

12. A process of claim 12 wherein the ratio of $SiO_2$ to $Al_2O_3$ in the catalyst is about 18–400.

13. A process of claim 2 wherein the total molar yield of pyridine, $\alpha$-picoline and $\beta$-picoline is at least about 75 molar percent, the weight ratio of pyridine to $\beta$-picoline in the product is about 1.8 to about 2.3 and the reaction is conducted at a temperature of about 425° C. to about 500° C. at which said yield and ratio are achieved.

14. A process of claim 2 wherein the total yield of pyridine, $\alpha$-picoline and $\beta$-picoline is from about 70 to less than 75 molar percent, the weight ratio of pyridine to $\beta$-picoline in the product is greater than about 2.3, and the reaction is conducted at a temperature of about 475° C. to about 650° C. at which said yield and ratio are achieved.

15. A process of claim 1 wherein the reactants comprise crotonaldehyde, formaldehyde and ammonia and the main product is pyridine.

16. A process of claim 1 wherein the reactants consist essentially of ammonia and acrolein; acrolein and acetaldehyde; acrolein and acetone; acrolein and propionaldehyde; propionaldehyde and formaldehyde; butyraldehyde, acetaldehyde and formaldehyde; butyraldehyde and formaldehyde; or acetaldehyde.

17. A process of claim 1 which is conducted at a temperature in a range in which the molar yield of total product and the weight ratio of principal product to side products are both essentially constant.

18. A process of claim 1 which is conducted at a temperature which is higher than a temperature range in which the molar yield of total product and the weight ratio of principal product to side products are both essentially constant; the resultant molar yield of total product being lower than that obtained when the reaction is conducted at a temperature in said range and said resultant weight ratio being higher than that obtained when the reaction is conducted at a temperature in said range.

19. A process of claim 1 wherein, in said catalyst, an amount up to 100% of the aluminum contained therein is replaced by a trivalent cation.

20. A process of claim 19, wherein the trivalent cation is boron.

21. A process of claim 19 wherein, in said catalyst, the trivalent cation is arsenic, antimony, vanadium, iron or chromium.

* * * * *